United States Patent [19]
Slocum

[11] Patent Number: 5,834,410
[45] Date of Patent: Nov. 10, 1998

[54] SURFACE TEXTURED CLEANSING DEVICE AND METHOD WITH MASSAGING EFFECT

[75] Inventor: Alexander H. Slocum, Bow, N.H.

[73] Assignee: AESOP, Inc., Concord, N.H.

[21] Appl. No.: 785,358

[22] Filed: Jan. 17, 1997

[51] Int. Cl.[6] .............................. C11D 9/00; C11D 17/04
[52] U.S. Cl. ................. 510/140; 510/142; 510/148; 510/159
[58] Field of Search .................... 510/140, 142, 510/148, 159, 439, 440, 449

[56] References Cited

U.S. PATENT DOCUMENTS

| | | | |
|---|---|---|---|
| 3,870,419 | 3/1975 | Sage | 401/8 |
| 4,222,676 | 9/1980 | Roth | 401/28 |
| 4,249,521 | 2/1981 | Gueret | 128/62 R |
| 4,469,094 | 9/1984 | Kaeser | 128/65 |
| 4,858,257 | 8/1989 | Bivens | 4/606 |
| 5,545,456 | 8/1996 | Suida | 428/76 |
| 5,582,581 | 12/1996 | Horton | 252/174 |

*Primary Examiner*—S. Mark Clardy
*Assistant Examiner*—Sabiha N. Qazi
*Attorney, Agent, or Firm*—Rines and Rines

[57] ABSTRACT

A bar of soap or soap dispensing container "bar", whereby teeth or ridges are formed into the product such that as it is rubbed on the body, the contact pressure causes the teeth to lightly bend the skin at a number of points creating a series of waves in the skin which move along the surface of the skin as the soap is moved, thereby creating a traveling wave which acts to help remove dirt and dead skin particles and create a pleasant massaging effect, wherein the teeth forms are shaped to provide transverse and lateral strength in the product so it will not easily break, and so that it can be stacked for more dense shipping and better handling.

14 Claims, 6 Drawing Sheets

SURFACE TEXTURED CLEANSING DEVICE AND METHOD WITH MASSAGING EFFECT

The present invention relates to soap bars including containers of liquid soap used as a "bar" being more particularly directed to the imbedding off such predicts with inherent massaging qualities.

BACKGROUND

There are a great many cleansing products on the market, and there are a great many brushes and washcloths that are often used with these products. In the case of a simple bar of soap, or liquid soap dispensed onto a person's hand, the soap acts as a lubricant, and thus glides over the skin such that cleaning action is primarily produced by chemical (surfactant action) means. To obtain greater cleaning action, many people use a washcloth or a brush which combines chemical cleaning action with the physical geometric cleaning action of scrubbing. However, the scrubbing action is often far too aggressive for people with sensitive skin. What is needed is a gentler means to create the geometric scrubbing action. In addition, there is also the issue of convenience. A washcloth must be laundered, and in a family, there is confusion as to the identity of ownership.

The solution set forth in the present invention is to form an appropriate geometric pattern of teeth in the soap, such that as the soap wears away, the pattern still remains. As the soap is pressed against the body, furthermore, the teeth indent the skin and create a traveling wave as the bar is passed over the skin. This traveling wave helps to shed particles, in much the same manner as bending the backing paper of an adhesive label to free the edge of the label. In addition, this wave creates a pleasant effect similar to that felt during a massage.

The present invention thus relates to creating features on the surface of a bar of soap, such that when the bar wears with use, the features are maintained, with the goal of creating a traveling wave on the skin as the body is rubbed with the bar, thereby producing a pleasing massage-like effect and creating a geometric wave that helps better to remove dead skin and dirt. Furthermore, the design can also be applied to a hollow plastic form "bar" that is filled or otherwise provided with liquid soap, which then flows slowly from or over the teeth as by hand pressure to the plastic bar, forcing the liquid soap out of tiny holes or through a porous membrane or the like.

OBJECT OF THE INVENTION

An object of this invention, accordingly, is to provide a new and improved bar of soap or the like.

A further object is to provide a novel bar of soap, having an appropriate geometric pattern of teeth formed in its surface such that when the soap is rubbed across the surface of the skin, the teeth indent into the skin and create a traveling wave that helps geometrically to shed particles in an assist to the chemical cleansing action provided by the soap itself.

A further object of the invention is to provide such a novel bar of soap or soap dispenser and method of dispensing and messaging in which the wave formed along the skin by rubbing the body with the soap dispenser also creates a pleasant massage-type feeling.

Additional objects are to provide a tooth form that maintains pattern during wear of the soap and provides strength in transverse directions of the bar to resist fracture when being used, or during manufacturing, shipping, or handling.

Still another object of the invention is to provide a tooth form that allows two bars of soap to be stacked face-to-face for attaining higher shipping densities.

A still further object of the invention is to apply the design concept to a hollow plastic form that is filled with liquid soap, which then flows slowly from the teeth via hand pressure to the plastic bar that forces the liquid soap out of tiny holes or through a porous membrane.

SUMMARY

In summary, the invention is concerned with special shaping of a bar of soap (or a liquid soap-dispensing container "bar"), with teeth or ridges such that as the bar is rubbed on the body, the contact pressure causes the teeth lightly to bend or deflect the skin, creating a series of waves in the skin which move along the surface of the skin as the bar is moved thereover, thereby creating a traveling wave which acts to help remove dirt and dead skin particles and synergetically creates a pleasant massaging effect. The teeth forms are shaped to provide transverse and lateral strength in the bar of soap so it will not easily break, and so that it can be stacked for more dense shipping and better handling. Furthermore, the design and technique can also be applied to a hollow plastic form "bar" that is filled with liquid soap, which then flows slowly from or around the teeth as in response to hand pressure to the plastic bar that forces the liquid soap out of tiny holes or through a porous membrane or the like.

The invention further provides a combined soap-providing and massage-generated bar of solid soap material having a user-holding back surface from which upwardly project a plurality of parallel teeth extending transversely across the bar and spaced from one another longitudinally along the bar.

Preferred and best mode embodiments are hereinafter described.

DRAWINGS

The invention will now be described with reference to the accompanying drawing in which.

THE INVENTION

Figure 1:
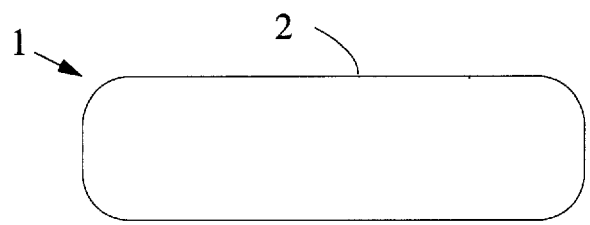
FIG. 1 is a side view of a traditional bar of soap.

FIG. 1 shows a conventional bar of soap 1 with a relatively flat surface 2, created to transfer soap suds to the skin or to a washcloth, but generally not at all engineered mechanically to interact with the body to enhance cleaning or the bathing experience. Perhaps this is due to historical carryover, when molds were to be made simple, and a bar of soap was meant to last for as long as possible. Today, however, greater emphasis is placed on consumer satisfaction; and although there are many soap formulations, all the soap bar shapes are still of the same basic rectilinear form, though some are slightly concave. Many people feel that a simple bar of soap, or a squirt of liquid soap alone, does not adequately clean the body well, and so people often use a washcloth or lufa or brush or the like—often too harsh for people with sensitive skins.

Figure 2:
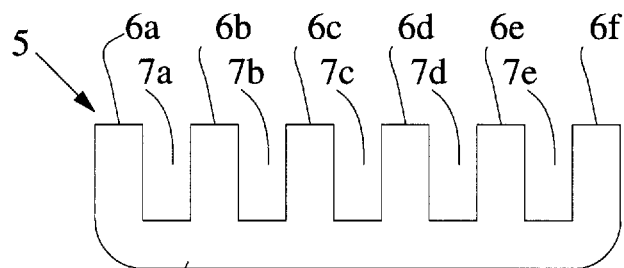
FIG. 2 is a side view of a soap bar provided in accordance with the invention with a toothed surface adapted to form a traveling wave in the skin.

FIG. 2 illustrates a new way to configure the shape of a bar of soap in accordance with the principles of the present invention, to address the above problems with conventional designs. A bar of soap 5 is shown configured to have a plurality of transversely extending spaced planar teeth 6a, 6b, 6c, 6d, 6e, and 6f with deep spaces 7a, 7b, 7c, 7d, and 7e between the teeth. The parallel spaced planar teeth are integrally joined at and project upwardly from the back of the soap in comb-like fashion, the back then fitting the palm of a user's hand.

Figure 3:
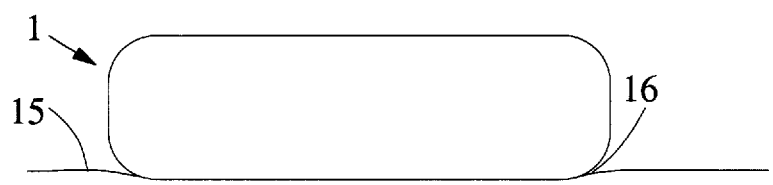
FIG. 3 is a schematic side view of such a traditional bar of soap in contact with the skin.

Comparing the action of this conventional bar 1 of FIG. 1 and the bar 5 of FIG. 2, FIG. 3 shows how the conventional bar of soap 1 floats on the surface of a person's skin 15, barely causing any deflection 16 of the skin because the force applied by a person's hand is distributed over such a large area. In addition, the broad flat contact zone builds up a hydrodynamic wedge which actually causes the bar of soap to glide over the surface of the skin, so that the soap acts like a lubricant and thus relies substantially solely on chemical cleansing action.

Figure 4:
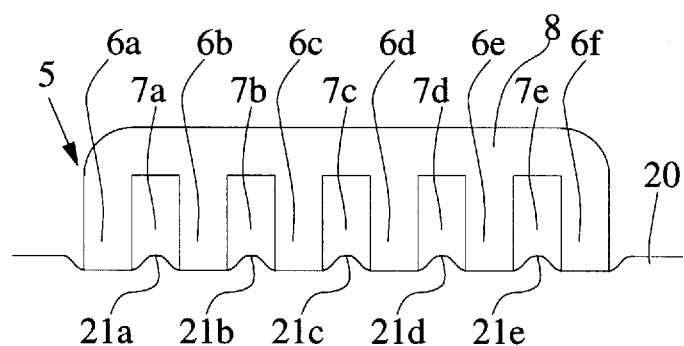
FIG. 4 is a schematic side view of the soap bar of FIG. 2 with the toothed surface in contact with the skin.

FIG. 4, on the other hand, shows how the transverse planar similar teeth 6a, 6b, 6c, 6d, 6e, and 6f of the bar 5 of the invention gently push into and deflect the surface of the skin 20 creating moving waves 21a, 21b, 21c, 21d, 21d, and 21e which protrude into the substantially equal spaces 7a, 7b, 7c, 7d, and 7e between the successive teeth in the soap surface. These traveling waves have changes in curvature as the bar passes over the skin which act to roll off dead skin particles and dirt from the skin surface. Thus, as the soap is rubbed horizontally along a person's skin, the force applied to the soap causes the transverse teeth on the surface of the soap lightly to bend the skin, generating a series of transverse waves in the skin which move along the surface of the skin as the soap is moved, thereby creating a traveling wave which helps remove dirt and dead skin particles.

The wave form moving across the skin not only helps to cleanse the skin, but it synergetically beneficially also provides a very pleasant massaging effect. The tooth form needed to create the optimal effect can be achieved with simple ridges formed into the soap bar surface, as tests have indicated, with the adaptability to form different types of ridges for different customer groups.

Figure 5:
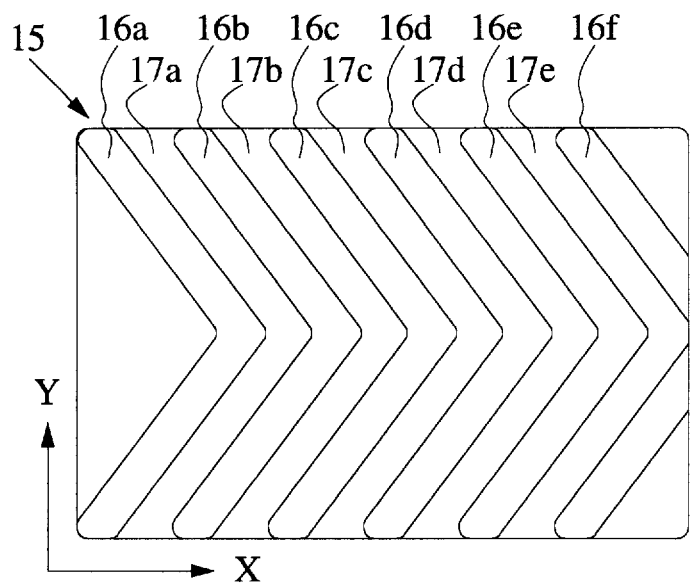
FIG. 5 is a top view of a preferred parallel spaced arrowhead toothed surface pattern which provides strength and allows for interlocking of bars.

While the forming of pure linear transverse ridges in the soap "comb", as in FIGS. 2 and 4, can achieve the desired cleansing and massaging effects, this construction requires the back body of the soap 8 to have sufficient thickness to prevent the soap from breaking as it is moved over the various body curves. It is accordingly deemed more desirable to adopt the tooth geometries shown in FIG. 5 or FIG. 6. In FIG. 5, parallel spaced V-shaped triangular or arrowhead or chevron spaced transverse ridge teeth are formed into the bar of soap 15 with a longitudinal spacing preferably slightly wider then the thickness of the ridges themselves. The triangular ridges 16a, 16b, 16c, 16d, 16e, and 16f overlap or interleave from tip to tail, such that they, in effect, allow the back body of the soap to span the distance between the ridges and remain strong when bending moments are applied about the X or Y axes. If two bars are stacked face-to-face, furthermore, they will be shifted by one tooth pitch, such that the teeth will fit in the spaces 17a, 17b, 17c, 17d, and 17e. While identical bars can be packaged, there will be some overhung extension, so it may sometimes be desirable to make mating top and bottom halves (i.e., FIG. 5 and a mating FIG. 5 with the ridges and spaces interchanged) that stack together to form what looks like a conventional bar of soap, for shipping.

A practical rectangular soap bar of the type shown in FIG. 5 may be of about 3½" long, 1¾a" wide, and having five V-angular teeth 16a each about ⅜" thick, spaced (17a) about ⁵⁄₁₆" apart (slightly wider than the tooth thickness, and with a tooth height of about ¾" above the back base, which was about ½" high (thick) to provide adequate strength during messaging. Rounding of the upper edges of the V-shaped planar teeth and of the bottom of the spaces at the base is preferred.

Figure 9:
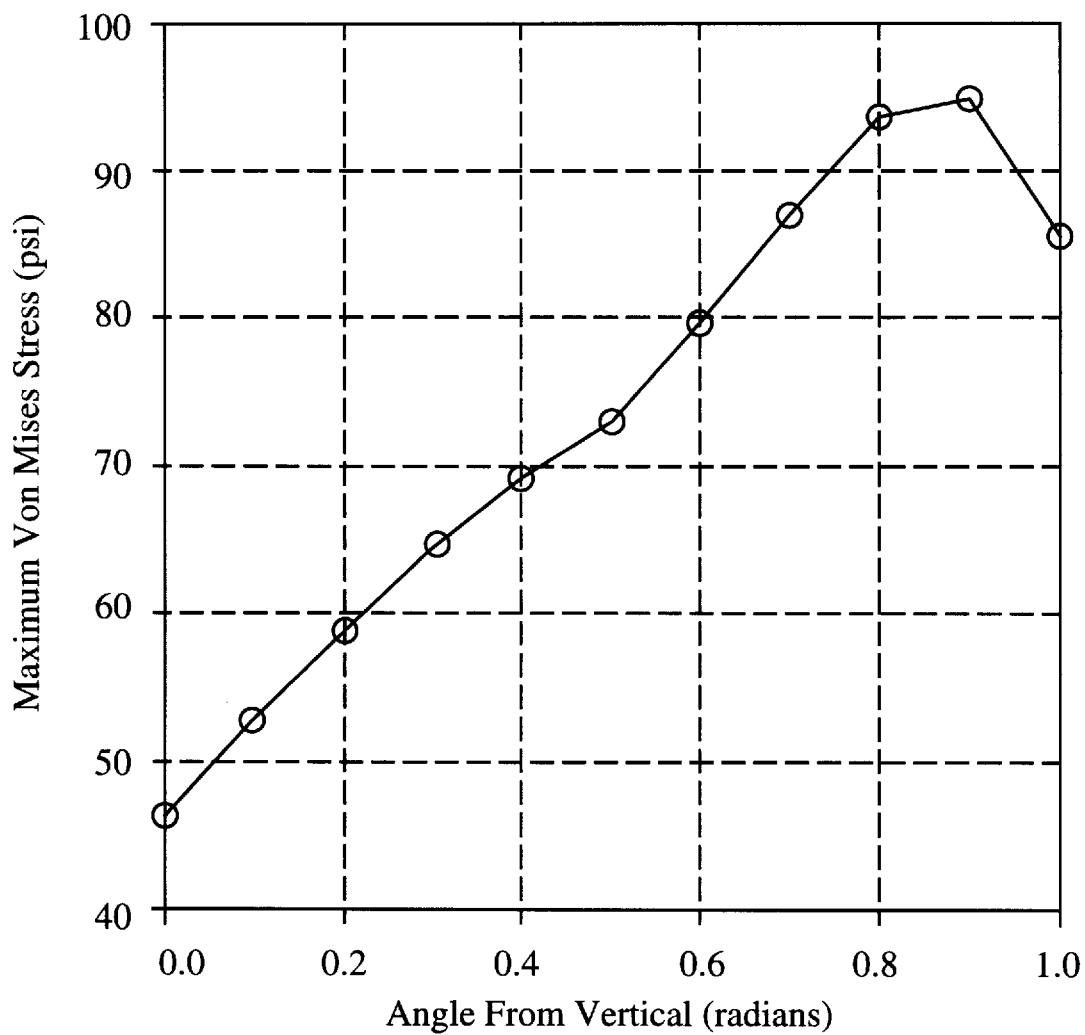
FIG. 9 is a plot of the stress in a bar of massage soap of the invention that shows the stress caused by the gripping action of a hand as a function of the angle of the stress-reducing chevron shapes.
Figure 10:
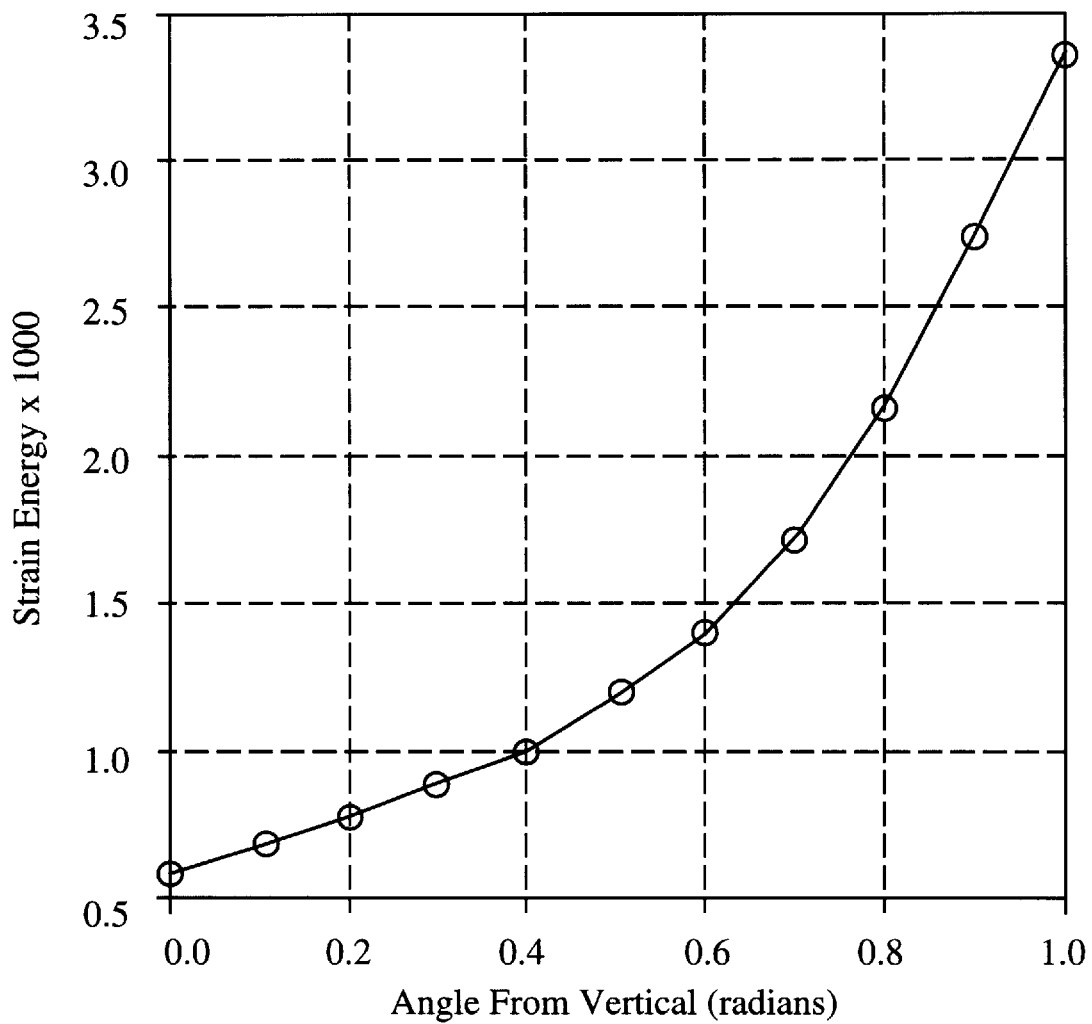
FIG. 10 is a plot of the strain energy in such a bar that shows the strain energy caused by the gripping action of a hand as a function of the angle of the stress-reducing chevron shapes.
Figure 11:
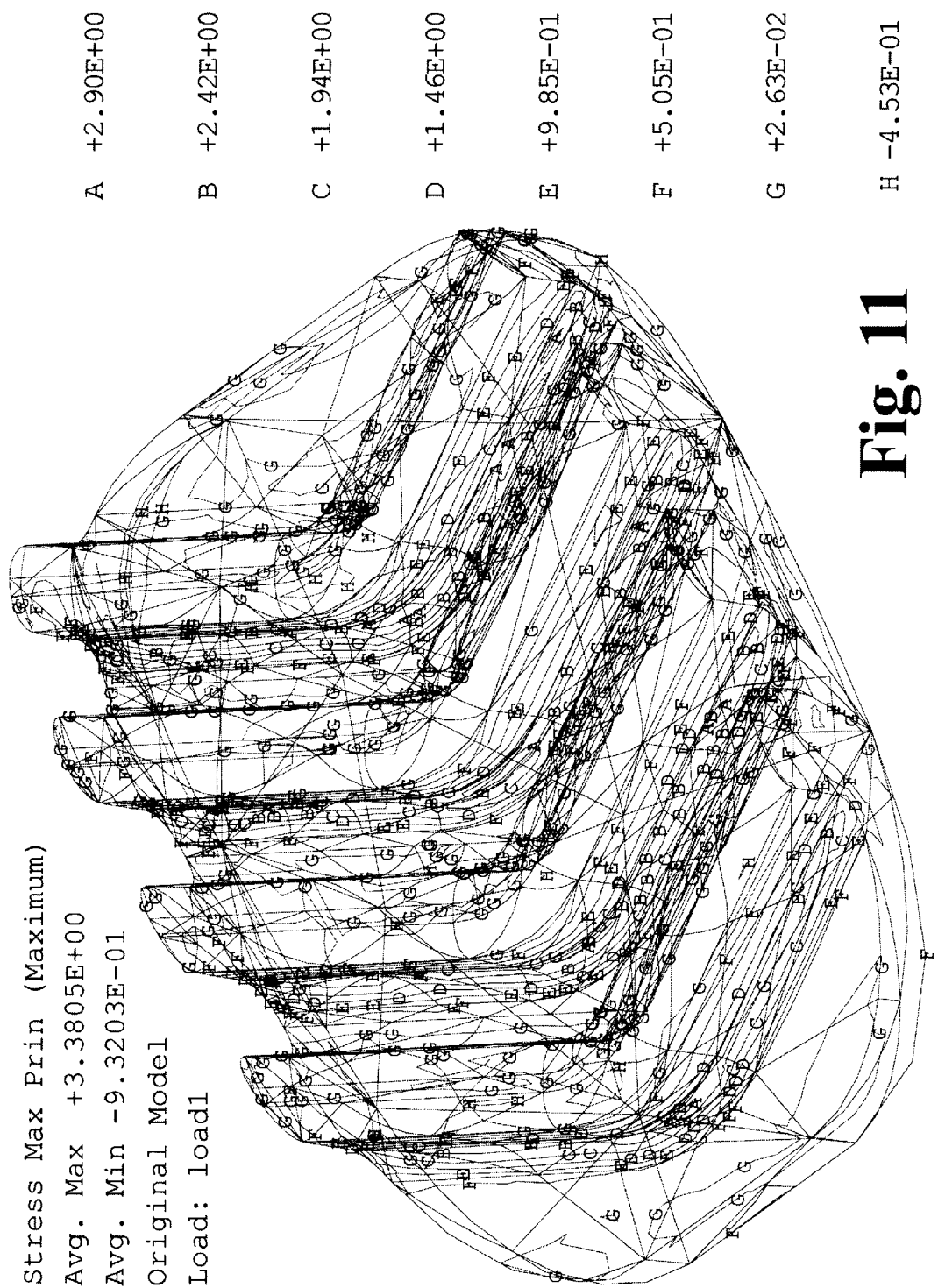
FIG. 11 is a contour plot of the stress from a finite element analysis of a bar that shows the stress caused by the gripping action of a hand.

In addition to experimental results, to confirm the effect of the chevron shapes such as 16 a, b, etc. in FIG. 5, finite element analysis was done for different angles of the chevrons. FIG. 9 is a plot of the stress in a bar so formed that shows the stress caused by the gripping action of a hand as a function of the angle of the stress reducing chevron shapes. It should be noted that as the angle becomes more shallow, the stress rises considerably (the discontinuity in the plot is due to the overall size of the bar, and the number of chevrons can change with the angle). FIG. 10 is a plot of the strain energy in such a bar that shows the strain energy caused by the gripping action of a hand as a function of the angle of the stress-reducing chevron shapes (e.g., chevron shapes 16a,b, etc. in FIG. 5). FIG. 11 is a contour plot of the stress from a finite element analysis, demonstrating the stress caused by the gripping action of a hand. These figures show that the chevrons act greatly to reduce the stress in such a bar, which allows the chevrons to be formed much deeper into the bar, resulting in longer effective life of the bar and greater customer satisfaction. A noted side benefit of the chevron shape, furthermore, is that the peak of the chevron enhances the massaging action.

While, as before discussed, various shapes of teeth or ridges may be used in accordance with the principles of the invention, the overlapping chevron design has been found preferable for enabling deep massaging profiles without introducing weakness which would cause the bar to split. The chevron concept can also be realized in personalized forms, such as undulating curves; and, as previously explained, can be arranged such that two blocks can fit in the space of one, or made double-sided such that unpacked blocks can be stacked.

Figure 6:
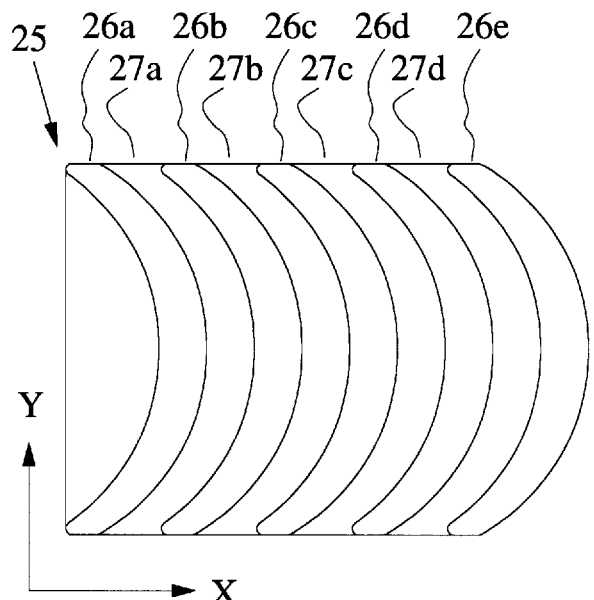
FIG. 6 is a top view of a modification illustrating a parallel spaced curved pattern which also provides strength and allows for interlocking of bars.

As before stated, FIG. 6 shows an arced parallel circular interleaved tooth version of the comb bar design, where the soap bar 25 has teeth 26a, 26b, 26c, 26d, and 26e, spaced by openings or valleys 27a, 27b, 27c, 27d. Since the arcs on the concave and convex sides of the teeth have the same radius of curvature, two bars will still stack face-to-face. Though the teeth are shown of square or rectangular cross-section, if structurally or ergonomically desirable, they may also be made to have other forms such as of trapezoidal shape, or the like.

These soap shapes can be made with conventional molding technology, and they can be packaged with conventional packaging equipment. The designs are robust and readily adaptable to yield greater bathing cleaning effectiveness, and greater user pleasure.

Figure 7:
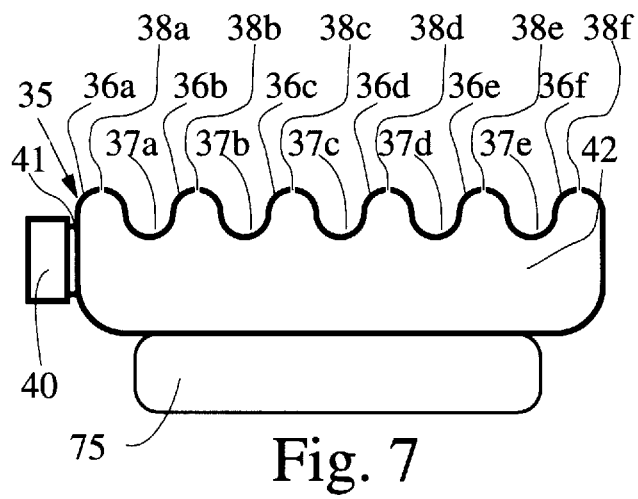
FIG. 7 is a side cross section view of a hollow plastic (e.g., blow molded) bar with massaging teeth-like bumps or ridges and that is filled with liquid soap for exuding through apertures in the bumps or ridges.

While the invention has been described in connection with a bar of solid soap material, the invention is not so limited, but may also be applied to a hollow plastic form "bar" that is filled with liquid soap, which then flows slowly from tiny apertures in the teeth in response to hand-squeezing pressure about the plastic bar that forces the liquid soap out of the tiny holes or through a porous membrane. The surface of the plastic teeth can thus be textured (smooth, light, medium, heavy) to suit the desires of the user or it may be combined with brush bristles or the like (not shown). The above is illustrated in FIG. 7 with what one might call a hollow fallible thick-toothed three dimensional comb-like "bar" 35. In this design, the product has the same shape as described before, but it comprises a hollow plastic "bar" form with spaced parallel rows of bumps (which could also be ridges as before in the soap bars) 36a, 37b, 36c, 36d, 36e, and 36f, with spaces 37a, 37b, 37c, 37d, and 37e between the bumps, and small holes or pores 38a, 38b, 38c, 38d, 38e, and 38f in the tips of the bumps. Liquid soap is filled into the container cavity 42 through a port 41 and capped with a cap 40. This design facilitates blow molding of the product, and the massaging teeth can either be in the form of ridges or discrete bumps such as spheres or the like, depending on the personal preference of the consumer—the design providing the flexibility for many different surface textures including attached brush bristles, as desired. In principle, the concept of massaging bumps with small soap-flow holes of FIG. 7 may also be applied to different forms of massage units such as rolling wheel or ball massagers, thus allowing for a great many different personal preferences to be accommodated.

Figure 8:
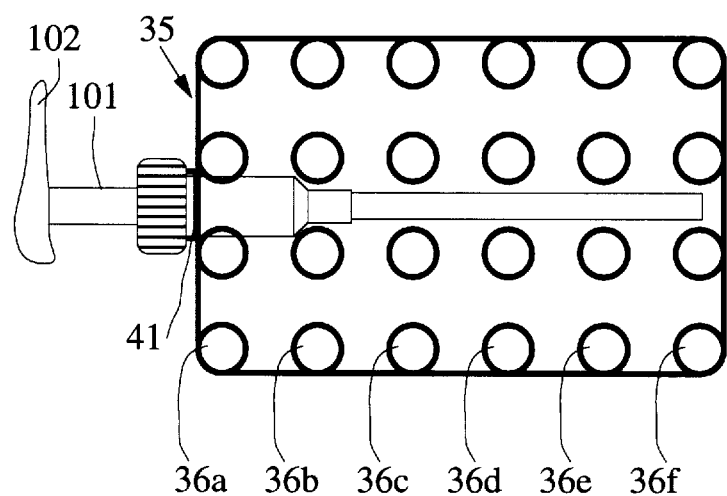
FIG. 8 is a top view of a modified hollow plastic (e.g., blow molded) bar with such massaging tooth-like bumps, that is filled with liquid soap from a pump dispenser.

FIG. 8 illustrates a further modification in which the container "bar" 35 has massaging teeth shown in bump form, one row labeled as 36a, 36b, 36c, 36d, 36e, and 36f, on the surface. In FIG. 8, holes are not used to distribute the soap, but instead, a soap pump 101 is used. The bottle may be held in the hand and the pump activated by the thumb, when needed. To prevent the nozzle 102 from gouging the skin, it may be made stubby and from a soft plastic such as PVC, as opposed to the hard nozzles commonly found on soap pumps. This design can also serve as a normal soap bottle, so the user may stand it up and use it either just to dispense soap, or as a massage "bar".

The concept of a massaging container design allows users to select a greater variety of soaps in liquid form, or even to blend fragrances with their favorite soap. The surface texture of the container "bar" teeth may be smooth, or micro-ridges may be molded into the teeth to get an extra micro-massage effect. It is even be possible to incorporate a water-tight vibration system into this design, such as on the back of the unit, to create an added soothing sensation while bathing, as shown in FIG. 7, where a waterproof battery powered vibrating unit 75 is added to the back of the "bar", permanently or detachably, so an actual bar of soap 5 may also be used in place of the textured container "bar" 35. The massaging ridges can also be made to cover the surface of a soap bar, or be formed into contour-fitting shapes, all of which are considered within the scope of this patent—in all cases providing a soothing massage while cleansing the skin.

Further modifications of the invention will also occur to persons skilled in the art, and all such are deemed to fall within the spirit and scope of the invention as defined by the appended claims.

What is claimed is:

1. A combined soap-providing and massage-generating bar of solid soap material having a user-holding back surface from which integrally upwardly project a plurality of solid soap material parallel teeth extending transversely across the bar and spaced from one another longitudinally along the bar.

2. A soap material bar as claimed in claim 1 and in which the height of the teeth is greater than the thickness of the back of the bar.

3. A soap material bar as claimed in claim 2 and in which the spacing between the teeth is slightly wider than the width of the teeth.

4. A soap material bar as claimed in claim 1 and in which the teeth are substantially planar.

5. A soap material bar as claimed in claim 4 and in which the teeth are shaped longitudinally to overlap.

6. A soap material bar as claimed in claim 5 and in which the teeth are substantially V-shaped ridges.

7. A soap material bar as claimed in claim 5 and in which the teeth are arcuate ridges.

8. A soap material as claimed in claim 1 and in which the height of the teeth is proportional relative to the thickness of the back of the bar to provide for the bar to be held at the back and rubbed over a user's body without fracture, and with the teeth creating deformation traveling waves along the body.

9. A soap material as claimed in claim 8 and in which the height of the teeth is greater than the thickness of the back of the bar to insure retention of the teeth as the soap is consumed.

10. A soap material as claimed in claim 1 and in which a vibrating pack is provided along the back of the bar.

11. A soap material bar as claimed in claim 1 and in which the same is assembled with an identical mating bar with the respective teeth and spaces interlocking.

12. A method of dispensing soap material and simultaneously generating massage action on a user's skin, that comprises, providing a soap bar integrally carrying a plurality of transversely extending parallel soap bar material projections closely spaced longitudinally from one another along the bar; and rubbing the projections along the user's skin with contact pressure that causes the projections lightly to bend the skin to create a series of traveling waves therealong.

13. A method as claimed in claim 12 and in which the transverse projections are shaped as longitudinally overlapping ridges to generate said waves.

14. A method as claimed in claim 13 and in which the soap dispensing is effected by a bar of soap in which ridges have been formed.

\* \* \* \* \*